United States Patent
Goto et al.

(10) Patent No.: US 6,465,657 B1
(45) Date of Patent: *Oct. 15, 2002

(54) METHOD OF PREPARING REFINED ORGANIC COMPOUND FOR USE IN PHOTOGRAPHY WITH IMPROVED LIQUID-LIQUID EXTRACTION FROM ORGANIC REACTION MIXTURE

(75) Inventors: Masayuki Goto; Noboru Tanaka, both of Odawara (JP)

(73) Assignee: Fuji Photo Film Co., Ltd., Kanagawa-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/537,719

(22) Filed: Mar. 30, 2000

(30) Foreign Application Priority Data

Mar. 30, 1999 (JP) ............................................. 11-089851

(51) Int. Cl.[7] ....................... C07D 487/06; C07C 255/50
(52) U.S. Cl. ..................................... 548/262.4; 558/404
(58) Field of Search ........................... 548/262.4, 267.6, 548/267.8; 558/411, 414, 418, 404

(56) References Cited

U.S. PATENT DOCUMENTS 4,705,863 A * 11/1987 Sato et al. ................... 548/262

FOREIGN PATENT DOCUMENTS

JP        A-4-230746        8/1992

* cited by examiner

Primary Examiner—Fiona T. Powers
(74) Attorney, Agent, or Firm—Birch, Stewart, Kolasch & Birch, LLP

(57) ABSTRACT

There is disclosed a method of preparing a refined organic compound, comprising the steps of adding water to an organic reaction mixture and mixing them, and then subjecting the mixture to filtration processing using a filter, to separate an organic phase from an aqueous phase, and then isolating the intended organic compound from said organic phase. The method enables highly precise removal of a water-easily soluble compound from an organic reaction mixture, and it further enables obtaining the intended synthesized organic compound in high yield with a high quality.

8 Claims, No Drawings

METHOD OF PREPARING REFINED ORGANIC COMPOUND FOR USE IN PHOTOGRAPHY WITH IMPROVED LIQUID-LIQUID EXTRACTION FROM ORGANIC REACTION MIXTURE

FIELD OF THE INVENTION

The present invention relates to a method of preparing the intended organic compound to be obtained, as a more refined product from an organic reaction mixture.

BACKGROUND OF THE INVENTION

It is well known that organic compounds to be used for photography and the like have various kinds of functional groups that exhibit intended photographic actions and functions, and they are obtained via steps of synthesis reaction. However, since the mixture thus obtained by way of these reactions generally contains a water-scarcely (sparingly) soluble compound and a water-easily soluble compound, it becomes important to prevent emulsion mixing and to efficiently carry out separation and purification. To separate the intended organic compound from the mixture, therefore, a variety of methods of obtaining the intended organic compound from the water-scarcely soluble compound while removing the water-easily soluble compound, have been proposed from the past.

As a typical method for removing such a water-easily soluble compound, a known method is separating the object, comprising steps of adding water to an organic reaction liquid, extracting a water-easily soluble substance in an organic reaction mixture into an aqueous phase, and then standing the liquid according to a separation method that utilizes the specific gravity difference between the phases, to thereby conduct phase separation into an organic phase and an aqueous phase, and then extracting the object from the organic phase (JP-A-4-230746, paragraphs 0052, 0061, etc.).

However, since the separation method by a specific gravity difference, which comprises standing a liquid, is low in separation efficiency, it causes such problems as that:

1) A water-easily soluble substance cannot be completely removed from an organic phase, which results in reduction in both the yield and quality of the object, and
2) Productivity of the object is low (it needs large-scale equipment and also requires much time).

SUMMARY OF THE INVENTION

Accordingly, an object of the present invention is to provide a method of highly precisely removing a water-easily soluble compound from an organic reaction mixture, and further obtaining the intended synthesized organic compound in a high yield with high quality.

Other and further objects, features, and advantages of the invention will appear more fully from the following description.

DETAILED DESCRIPTION OF THE INVENTION

As a result of intensive investigation to achieve the above-described object, this inventor has found that an organic phase, which is a continuous phase, and an aqueous phase can be separated from each other with high precision by adding water into a reaction mixture containing a mixture of organic chemicals and mixing them, so that a fixed amount of water exists therein, and thereby compulsively accelerating the growth of liquid droplets (water particles) in the reaction mixture, and consequently accelerating filtration of the mixture using a filter, and further that the intended organic compound can be isolated from the thus-separated organic phase in a high yield with high quality. The present invention has been made based on the above-mentioned novel knowledge.

That is, the present invention provides the following production methods:

(1) A method of preparing a refined organic compound, comprising the steps of adding water to an organic reaction mixture and mixing them, and then subjecting the mixture to filtration processing using a filter, to separate an organic phase from an aqueous phase, and then isolating the intended organic compound from said organic phase.

(2) The method of preparing a refined organic compound as described in the above (1), wherein a produced organic compound in the organic reaction mixture is water-scarcely soluble and has a molecular weight of 300 to 1500.

(3) The method of preparing a refined organic compound as described in the above (2), wherein the produced organic compound is selected from photographic chemicals such as a photographic coupler, a coloring matter for instant photography, and an antifoggant.

(4) The method of preparing a refined organic compound as described in the above (1), wherein the mixing weight ratio of the organic reaction mixture to water is 1: (0.5 to 2).

(5) The method of preparing a refined organic compound as described in the above (1), wherein the mixing of the organic reaction mixture and water is carried out using a stirrer or a static-type mixer.

(6) The method of preparing a refined organic compound as described in the above (1), wherein the filter is fibrous and exhibits a pore size of 3 $\mu$m to 30 $\mu$m.

According to the method of the present invention, an organic reaction mixture, obtained by a synthesis reaction, is dissolved in a water-scarcely soluble organic solvent. The term "water-scarcely soluble organic solvent" herein used, means an organic solvent that dissolves the intended organic compound but that is not arbitrarily blended with water. The solubility of the water-scarcely soluble organic solvent for use in the present invention to water is 15 weight % or less, preferably 10 weight % or less, most preferably 5 weight % or less, and especially preferably 0.1 weight % or less, at 25° C. Examples of the water-scarcely soluble organic solvent include ethyl acetate, isopropyl acetate, methylethylketone, butyl acetate, methylene chloride, toluene, cyclohexanone, and n-hexane. Further, a mixture of these solvents may be used. The amount of the water-scarcely soluble solvent to be added is preferably 1 to 10 weight times, more preferably 2 to 8 weight times, and especially preferably 3 to 7 weight times, the unit weight amount (1 kg) of the intended organic compound.

When an organic reaction mixture just after synthesis is obtained as a solution that has dissolved it in a water-scarcely soluble organic solvent, which serves as a reaction solvent, the step of adding the water-scarcely soluble organic solvent (e.g. toluene) according to the present invention has already been completed. Examples of the water-easily soluble compounds that are contained in an organic reaction mixture just after synthesis, include a solvent that can be arbitrarily blended with water, such as dimethylacetamide, dimethylformamide, acetone, methanol, and ethyleneglycol, each of which is used as a reaction solvent, and further, various kinds of acids, such as hydrochloric acid, sulfurous acid, sulfic acid, and nitric acid, each of which is formed in the course of reaction, and salts thereof.

The viscosity of the organic reaction mixture is preferably 1 to 20 centipoise, more preferably 3 to 15 centipoise, and especially preferably 5 to 10 centipoise. The term "viscosity" herein used indicates a value obtained by measurement at room temperature (20° C.), using, for example, the B-type viscometer Model RB-80L, manufactured by Toki Sangyo Co. Ltd.

Next, according to the method of the present invention, water is added to an organic reaction mixture containing a water-scarcely soluble solvent, followed by mixing.

The addition amount of water to be used is preferably 0.1 to 10 weight times, more preferably 0.2 to 5 weight times, and especially preferably 0.5 to 2 weight times, the unit weight amount (1) of the organic reaction mixture. Washing of the organic reaction mixture is also carried out by the addition of water.

As the mixing method of the organic reaction mixture and water, though it is not especially limited, mixing by a stirrer or a rest-type mixer is preferred. The timing of the start of mixing may be while adding water, or after water has been introduced into the organic reaction mixture.

In the present invention, the organic reaction mixture and water are mixed to the extent that droplets of the intended organic compound, as a result of mixing, are dispersed in the size of preferably 0.1 to 50 μm, and more preferably 5 to 20 μm.

Next, once a liquid in which an organic chemical mixture and water are dispersed, is allowed to pass through a filter, dispersed droplets aggregate and grow to a size of not less than 0.1 mm. As a result, an organic phase and an aqueous phase rapidly separate from each other. As the filter, porous films are generally used. Examples of the filter include a cloth, a nonwoven fabric, a wire gauze, a column packed with small particles, a sintering metal, and sintering ceramics of these filters, a fibrous nonwoven fabric is especially preferred. As the quality of the material used, polyvinylchloride, polyvinylidenechloride, bromix fiber, polyamide (Nylon), polyester, polyethylene, polypropylene, polyethylenephthalate, glass wool, and cotton are preferred.

The pore size of the filter is preferably 0.1 to 50 μm, and more preferably 3 to 30 μm. The pore size of the fibrous filter is preferably 5 to 30 μm.

The form of the filter is not especially limited, and therefore the filter can be used in any form, such as plain film-like, cylinder-shaped, capillary-shaped, spiral, and pleat-shaped forms. However, it is preferable that the filter be used in the form of a pleat-shaped cartridge, from the viewpoint of processing efficiency. As for a cartridge-shaped filter, it is possible to enhance the separation capacity and increase the passing velocity by forming a multilayer structure, in which the pore size of the interior is made fine (preferably 5 to 10 μm), whereas that of the exterior is made coarse (preferably 20 to 30 μm). Further, it is possible to attain similar effects by making a difference in fiber density between the interior and the exterior of the cartridge, i.e. making the interior dense (preferably 0.2 to 0.3 g/cm$^3$) while making the exterior rough (preferably 0.05 to 0.15 g/cm$^3$).

Next, according to the present invention, the aqueous phase thus separated after having the mixture solution passed through a filter, is removed, and then the object is obtained from an organic phase. As a method of obtaining the object, though it is not especially limited, solidification (caking) by distilling off a solvent, and crystallization by allowing crystals to be deposited, are preferred. Further, the object can also be isolated as a solution without solidifying it.

The method of the present invention enables highly precise removal of a water-easily soluble compound from an organic reaction mixture, and it further enables obtaining the intended synthesized organic compound in high yield with a high quality.

Hereinbelow, the present invention is described in more detail based on the following examples.

EXAMPLE

Example 1

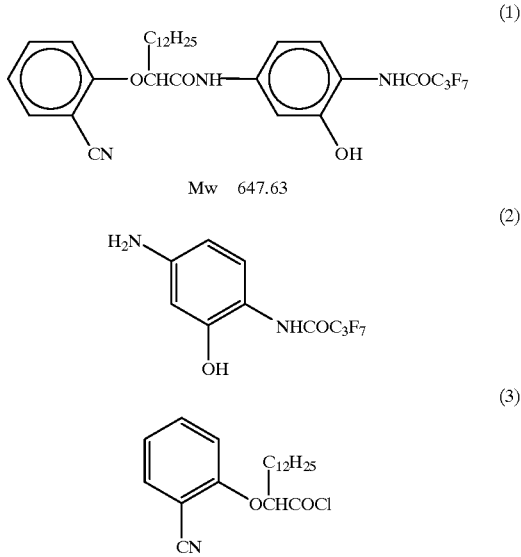

In order to obtain a cyan coupler having the chemical structure shown in the above-described (1), the following tests were carried out.

19.7 g of the amine (compound (2)) was dissolved in 70 ml of ethyl acetate, and the solution was allowed to be stirred while cooling at 0 to 5° C. To the resultant solution, a solution of 21 g of carboxylic acid chloride (compound (3)) in 50 ml of ethyl acetate was added, dropwise. Thereafter, the mixture was stirred for 1 hour at 0 to 5° C., to obtain an organic reaction mixture containing the desired compound (1).

120 ml of water was added to the resultant reaction solution, and the mixture was allowed to be stirred for 10 min., for mixing. As a result, droplets were grown to the size of 10 μm.

The mixture liquid was passed through a pleat-shaped cartridge filter composed of a polyethylene fiber nonwoven fabric having pores with a size of 10 μm, so that the organic phase and the aqueous phase were separated from each other.

The water content of the organic phase was measured. Measurement of the water content was carried out using a moisture meter AQV-7, manufactured by Hiranuma Sangyo Co. Ltd.

As a comparative example, 120 ml of water was added to the reaction solution, and the mixture was stirred for mixing.

Thereafter, the mixture liquid was left standing, for separation. After 1 hour, the water content of an organic phase was measured. The results are shown below.

|  | Water Content of Organic Phase |
| --- | --- |
| Example 1 | 1,100 ppm |
| Comparative Example | 7,000 ppm |

The results indicated above show that the water density in the organic phase, separated by the method of the Example 1 according to the present invention, is preferably low.

Ethyl acetate was distilled off from the above organic solution under reduced pressure, to obtain the solid containing compound (1), in an amount of 35 g (purity: 98%).

Comparative Example 1

The cyan coupler (1) was synthesized in the same manner as in Example 1, except for skipping the step of adding 120 ml of water to the reaction solution. Thereafter, the reaction mixture was passed through the same polyethylene filter as in Example 1. As a result, only the organic phase was obtained. Ethyl acetate was distilled off from the above-described organic solution under reduced pressure in the same manner as in Example 1, to obtain the solid-containing compound (1), in an amount of 40.7 g (purity: 84%).

Example 2

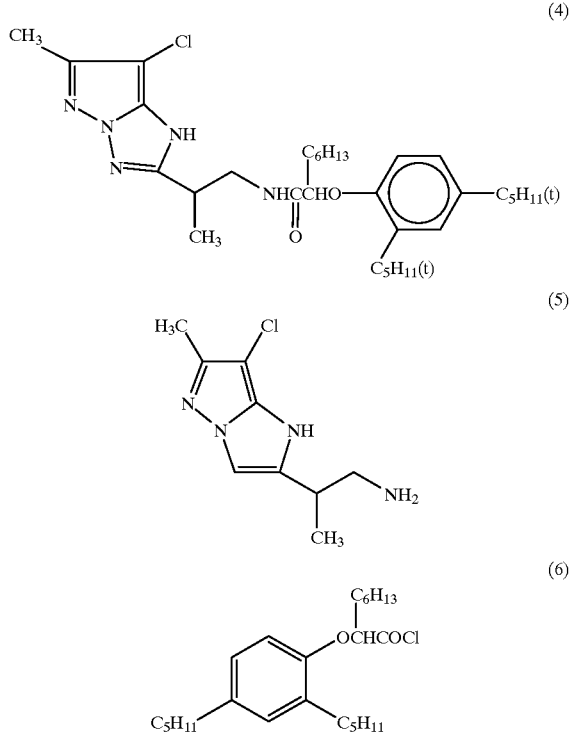

In order to obtain the magenta coupler having the chemical structure shown in formula (4), the following tests were carried out.

19.7 g of the amine (compound (5)) was dissolved in 20 ml of diethylformamide, and the solution was allowed to be stirred while cooling at 0 to 5° C. To the resultant solution, 19.5 g of the carboxylic acid chloride (compound (6)) was added, dropwise. Thereafter, the mixture was stirred for 1 hour at 10° C. or less, to obtain an organic reaction mixture containing the compound (4).

150 ml of toluene was added to the resultant reaction solution, and the solution was stirred for 10 min., for mixing.

Next, 180 ml of water was added, and the mixture was stirred for 10 min., for mixing. As a result, droplets were grown to the size of 8 $\mu$m.

The mixture liquid was passed through a cartridge filter composed of two layers, i.e. an inner layer made of a pleat-shaped polyethylene terephthalate fiber nonwoven fabric having a pore size of 5 $\mu$m, and an outer layer made of a cotton fiber nonwoven fabric exhibiting a pore size of 20 $\mu$m, and consequently the mixture was separated into an organic phase and an aqueous phase. Thereafter, the water content of the organic phase was measured. Measurement of the water content was carried out using a moisture meter AQV-7, manufactured by Hiranuma Sangyo Co. Ltd.

As a comparative example, 180 ml of water was added to the reaction solution, and the mixture was stirred for 10 min., for mixing. Thereafter, the mixture liquid was stood for separation. After 1 hour, the water content of the organic phase was measured. The results are shown below.

|  | Water Content of Organic Phase |
| --- | --- |
| Example 2 | 800 ppm |
| Comparative Example 2 | 5400 ppm |

Toluene was distilled off from the above-described organic solution under reduced pressure. Thereafter, the resultant concentrate was dissolved with 150 ml of acetonitrile. Then, crystallization was conducted at 20° C., followed by filtration, to obtain the compound (4), in an amount of 27 g (purity: 99%).

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of preparing a refined organic compound, comprising the steps of:
   adding water to an organic reaction mixture, said organic reaction mixture contains an organic compound which is selected from a group of photographical chemicals consisting of a photographic coupler, a coloring matter for instant photography, and an antifoggant,
   mixing the organic reaction mixture,
   filtering the organic reaction mixture through a filtration process, to separate an organic phase from an aqueous phase, and
   isolating the organic compound from said organic phase.
2. The method for preparing a refined organic compound as claimed in claim 1, wherein the organic compound in the organic reaction mixture is water-scarcely soluble and has molecular weight of 300 to 1500.
3. The method of preparing a refined organic compound as claimed in claim 1, wherein the mixing weight ratio of the organic reaction mixture and water is 1:0.5 to 1:2.
4. The method of preparing a refined organic compound as claimed in claim 1, wherein the mixing of the organic reaction mixture and water is carried out using a stirrer or static mixer.

5. A method of preparing a refined organic compound comprising the steps of:
- adding water to an organic reaction mixture, said organic reaction mixture contains an organic compound which is selected from a group of photographical chemicals consisting of a photographic coupler, a coloring matter for instant photography, and an antifoggant,
- mixing the organic reaction mixture,
- filtering the organic reaction mixture through a filtration process, to separate an organic phase from an aqueous phase, and
- isolating the organic compound from said organic phase, wherein the filter is fibrous and exhibits a pore size of 3 $\mu$m to 30 $\mu$m.

6. A method of preparing a refined organic compound, comprising the steps of:
- adding water to an organic reaction mixture dissolved in a water-scarcely soluble organic solvent, said organic mixture contains an organic compound, which is a photographic chemical, and is water-scarcely soluble and has a molecular weight of 300 to 1500;
- mixing the organic reaction mixture;
- filtering the organic reaction mixture through a filtration process to separate an organic phase from an aqueous phase; and
- isolating the organic compound from said organic phase.

7. The method according to claim 6, wherein the water-scarcely soluble organic solvent is selected from the group consisting of ethyl acetate, isopropyl acetate, methylethylketone, butyl acetate, methylene chloride, toluene, cyclohexanone, n-hexane and combinations thereof.

8. A method of preparing a refined organic compound comprising the steps of adding water to an organic reaction mixture and mixing them, and then subjecting the mixture to filtration processing using a filter, to separate an organic phase from an aqueous phase, and then isolating the intended organic compound from said organic phase, wherein the filter is fibrous and exhibits a pore size of 3 $\mu$m to 30 $\mu$m.

* * * * *